US007413740B2

(12) United States Patent
Sawada et al.

(10) Patent No.: US 7,413,740 B2
(45) Date of Patent: Aug. 19, 2008

(54) CHOLESTEROL-LOWERING AGENTS, SECONDARY BILE ACID PRODUCTION INHIBITORS AND FOODS AND DRINKS

(75) Inventors: Haruji Sawada, Tokyo (JP); Yasuto Yoshida, Tokyo (JP); Yasue Wada, Tokyo (JP); Kenji Ohishi, Tokyo (JP); Masahiko Itoh, Tokyo (JP); Wakae Yokoi, Tokyo (JP); Tunekazu Watanabe, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 307 days.

(21) Appl. No.: 11/176,398

(22) Filed: Jul. 8, 2005

(65) Prior Publication Data

US 2005/0244426 A1    Nov. 3, 2005

Related U.S. Application Data

(62) Division of application No. 10/031,569, filed as application No. PCT/JP00/04843 on Jul. 19, 2000, now Pat. No. 7,101,544.

(30) Foreign Application Priority Data

Jul. 21, 1999 (JP) ................................. 11-206218
Mar. 10, 2000 (JP) ................................. 2000-66659

(51) Int. Cl.
*A61K 36/06* (2006.01)
(52) U.S. Cl. ................................. 424/195.16
(58) Field of Classification Search ............. 424/195.16
See application file for complete search history.

(56) References Cited

U.S. PATENT DOCUMENTS

| 3,995,066 | A |   | 11/1976 | Muys et al. |
| 4,251,519 | A |   | 2/1981  | Robbins et al. |
| 4,313,934 | A |   | 2/1982  | Kitamura et al. |
| 4,530,846 | A |   | 7/1985  | Nagodawithana et al. |
| 4,716,115 | A |   | 12/1987 | Gonzalez et al. |
| 4,739,046 | A |   | 4/1988  | Di Luzio |
| 4,740,593 | A |   | 4/1988  | Gonzalez et al. |
| 4,891,220 | A |   | 1/1990  | Donzis |
| 5,622,843 | A | * | 4/1997  | Day et al. ............ 435/69.6 |
| 5,679,557 | A |   | 10/1997 | Ito et al. |
| 5,811,293 | A |   | 9/1998  | Furukawa et al. |
| 6,284,243 | B1 |  | 9/2001  | Masuyama et al. |

FOREIGN PATENT DOCUMENTS

| EP | 462021     | 12/1991 |
| JP | 50-68867   | 6/1975  |
| JP | 60-94077   | 5/1985  |
| JP | 60-251857  | 12/1985 |
| JP | 62-58987   | 3/1987  |
| JP | 2-286057   | 11/1990 |
| JP | 3-30667    | 2/1991  |
| JP | 04-049243  | 2/1992  |
| JP | 5-211859   | 8/1993  |
| JP | 6-62836    | 3/1994  |
| JP | 8-298982   | 11/1996 |
| JP | 9-23848    | 1/1997  |
| JP | 9-107919   | 4/1997  |
| WO | WO 92/13896 | 8/1992 |
| WO | WO 96/28476 | 9/1996 |

OTHER PUBLICATIONS

E. G. Offenbacher, et al., Diabetes, vol. 29, pp. 919-925, "Beneficial Effect of Chromium-Rich Yeast on Glucose Tolerance and Blood Lipids in Elderly Subjects", Nov. 1980.
E. G. Offenbacher, et al., The American Journal of Clinical Nutrition, vol. 42, No. 3, pp. 454-461, "The Effects of Inorganic Chromium and Brewer's Yeast on Glucose Tolerance, Plasma Lipids, and Plasma Chromium in Elderly Subjects [1-4]", Sep. 1985.
A. T. Hostmark, et al., The Journal of Nutrition, vol. 109, No. 6, pp. 1073-1078, "Plasma Lipid and Lipoprotein Responses of Rats to Starch and Sucrose Diets With and Without Brewer's Yeast[1]", 1978.
J. DeAbreu, et al., Archivos Latino Americanos De Nutricion, vol. 44, No. 1, pp. 18-22, "Effect of Addition of Brewer's Yeast to Soy Protein and Casein on Plasma Cholesterol Levels of Rabbits", 1994.
S. Cho, et al., Bulletin of the Faculty of Home Life Science, Fukuoka Women's University, vol. 16, pp. 65-69, "Effect of Polysaccharide Produced by *Bacillus natto* or Alcohol Extract of Yeast on the Lipid Metabolism of Rats", Sep. 30, 1984.
T. Kishida, Journal of Japanese Society of Food and Nutrition, vol. 26, pp. 371-375, "On the Serum Cholesterol-Lowering Effect of *Saccharomyces cerevisiae* Liquid Culture", 1973.
T. Narisawa, et al., Journal of the National Cancer Institute, vol. 53, No. 4, pp. 1093-1097, "Promoting Effect of Bile Acids on Colon Carcinogenesis After Intrarectal Instillation of N-Methyl-N'-Nitro-N-Nitrosoguanidine in Rats [1,2]", Oct. 1974.
H. Tsuda, et al., Gann, vol. 75, No. 10., pp. 871-875, "Promotive Effect of Primary and Secondary Bile Acids on the Induction of γ-Glutamyl Transpeptidase-Positive Liver Cell Foci as a Possible Endogenous Factor for Hetatocarcinogenesis in Rats", Oct. 1984.
T. Makino, et al., J. Natl. Cancer Inst., vol. 76, No. 5, pp. 967-975, "Effects of Phenobarbital and Secondary Bile Acids on Liver, Gallblader, and Pancreas Carcinogenesis Initiated by N-Nitrosobis(2-Hydroxypropyl)Amine in Hamsters [1,2]", May 1986.
B. S. Reddy, et al., Cancer Research, vol. 37, pp. 3238-3242, "Promoting Effect of Bile Acids in Colon Carcinogenesis in Germ-Free and Conventional F344 Rats[1]", Sep. 1977.
S. N. Marcus, et al., Gut, vol. 29, No. 4, pp. 522-533, "Deoxycholic Acid and the Pathogenesis of Gall Stones", Apr. 1988.
T. S. Low-Beer, et al., The Lancet, vol. 2, No. 8099, pp. 1063-1065, "Colonic Bacterial Activity, Biliary Cholesterol Saturation, and Pathogenesis of Gallstones", Nov. 18, 1978.

(Continued)

*Primary Examiner*—Herbert J Lilling
(74) *Attorney, Agent, or Firm*—Oblon, Spivak, McClelland, Maier & Neustadt, P.C.

(57) ABSTRACT

Secondary bile acid production inhibitors and cholesterol-lowering agents containing a yeast as the active ingredient.

11 Claims, 1 Drawing Sheet

OTHER PUBLICATIONS

A. Roda, et al., Journal of Pharmaceutical Sciences, vol. 81, No. 3, pp. 237-240, "Effect of Basic Cholane Derivatives on Intestinal Cholic Acid Metabolism: In Vitro and In Vivo Activity," Mar. 1992.

F. M. Nagengast, et al., European Journal of Clinical Investigation, vol. 18, pp. 56-61, "Inhibition of Secondary Bile Acid Formation in the Large Intestine by Lactulose in Healthy Subjects of Two Different Age Groups", 1988.

J. W. Lampe, et al., Gut, vol. 34, pp. 531-536, "Sex Differences in Colonic Function: A Randomised Trial", 1993.

J. Seikagaku, 1st Printing, pp. 804-805, "Biosynthesis of Bile Acid", 1984 (with English translation).

Kazutomo Imahori et al., ed.: "Seikagaku Jiten" Kabushiki Kaisha Tokyo Kagaku Doujin (1st printing in 1984) p. 736 "biosynthesis of bile acid".

Patent Abstracts of Japan, JP 62-016424, Jan. 24, 1987.

Patent Abstracts of Japan, JP 62-129223, Jun. 11, 1987.

Patent Abstracts of Japan, JP 09-077674, Mar. 25, 1997.

* cited by examiner

CHOLESTEROL-LOWERING AGENTS, SECONDARY BILE ACID PRODUCTION INHIBITORS AND FOODS AND DRINKS

This application is a DIV of Ser. No. 10/031,569 Jan. 22, 2002 U.S. Pat. No. 7,101,544 which is a 371 of PCT/JP00/04843 Jul. 19, 2000 which claims benefit to JAPAN 11-206218 Jul. 21, 1999 and JAPAN 2000-66659 Mar. 10, 2000.

TECHNICAL FIELD

The present invention relates to a cholesterol-lowering agent capable of lowering the blood or hepatic cholesterol level and improving atherogenic index; to a secondary bile acid production inhibitor useful for preventing and treating colorectal cancer, liver cancer, pancreatic cancer, cholelithiasis, etc.; and to use thereof for producing foods and drinks.

BACKGROUND ART

In recent years, the mortality rate relating to cardiovascular diseases has increased year by year. If diseases caused by arteriosclerosis such as cardiac infarction and brain infarction are included, cardiovascular diseases are ranked at the top of the causes of death in adults.

Arteriosclerosis is caused by a variety of factors. Among them, increase in plasma lipid level, inter alia, plasma cholesterol level, is conceivably one of the most dangerous factors.

One cause of elevated plasma cholesterol level is a genetic disease. In this case, grave patients are given diet therapy, and simultaneously, drugs such as a cholesterol synthesis inhibitor, Nicomol, Clofibrate, an ion-exchange resin, and an anabolic steroid are employed. However, these drugs cause adverse side effects such as toxicity to the liver, gastrointestinal disorders, and carcinogenicity.

Another important cause of elevated plasma cholesterol level is excessive fat consumption caused by the recent dietary custom of consuming a large quantity of eggs, butter, meat, etc., to the extent that excessive fat consumption has become the general habit for younger people. Alimentary hypercholesterolemia induced by excessive fat consumption generally does not become grave in comparison with that caused by genetic factor. But alimentary hypercholesterolemia induces a gradual accumulation of cholesterol in the vascular wall from a young age and problematically causes arteriosclerosis in adulthood, and then may cause cardiac infraction and brain infraction together with hypertriglyceridemia. In relation to these hyperlipemias, diet therapy including limitation of lipid consumption within an appropriate range is of great importance, rather than drug therapy, which raises problems such as adverse side effects. However, patients under diet limitation suffer mental pain and must abandon the joy of their regular diet. Thus, complete diet therapy is difficult to attain, and the effect thereof is usually limited.

Excessive cholesterol in plasma accumulates on the inside of the blood vessels, inducing arteriosclerosis. However, if the cholesterol is taken up in the liver, and, then cholesterol and its metabolites, namely bile acid are excreted into the intestiral track without accumulation in the liver, followed by discharge together with feces to outside the body, the pool oize of cholesterol in the body decreases, to thereby prevent arteriosclerosis onset by the aforementioned mechanism. Thus, a cholesterol-lowering agent which exerts an effect for lowering hepatic cholesterol level as well as plasma cholesterol level has been desired.

A variety of microorganisms exerting a cholesterol-lowering effect with slight side effects are disclosed. However, yeasts are disclosed in surprisingly few number. From long ago, brewer's yeast has been known as a typical yeast, and its effect of improving lipid metabolism is disclosed in several literatures. For example, there are disclosed a case in which administration of chromium-added brewer's yeast (9 g/day) for eight weeks to elderly subjects decreased the serum cholesterol level [Ester G. Offenbacher and F. Xavier Pi-Sunyer, Beneficial effect of chromium-rich yeast on glucose tolerance and blood lipids in elderly subjects. *Diabetes,* 29, 919, (1980)]; a case in which administration of chromium chloride and brewer's yeast (5 g) for 10 weeks to elderly subjects caused no effect on the serum cholesterol level and triacylglycerol level [Caral J. Rinko, and F. Xavier Pi-Sunyer, The effects of inorganic chromium and brewer's yeast on glucose tolerance, plasma lipids, and plasma chromium in elderly subjects., *Am. J. Clin. Nutr.,* 42, 454, (1985)]; and a case in which administration test of no-chromium-added brewer's yeast to human subjects resulted in no effect of lowering the serum cholesterol level [Arne T. Hostmark, Einar Eilertsen, and Ole Gronnerod, Plasma lipid and lipoprotein responses of rats to starch and sucrose diets with and without brewer's yeast., *J. Nutri.,* 109, 1073, (1978)]. In addition, there is disclosed a case in which administration of a soybean-protein-added diet lowered the serum cholesterol level of rats, but a slight increase in the level was attained when 50% of the soybean protein was substituted by brewer's yeast [Jorge De Abreu and Nancy Millan, Effect of addition of brewer's yeast to soy protein and casein on plasma cholesterol levels of rabbits. *Archivos Latinoamericanos de Nutricion.,* 44, 18, (1994)].

As described above, at present, there still remain different theories regarding the effect of brewer's yeast on improvement of lipid metabolism.

Effects of other yeasts are also disclosed in literature. For example, a methanol extract of *Sporobolomyces ruberrinus* and that of *Saccharomyces uvarum* are reported to slightly lower the serum cholesterol level and triglyceride level of choresterol-loaded rats (Shuji CHO, Hisao FUJII, and Jun Shiraishi, Effect of polysaccharide produced by *Bacillus natto* or alcohol extract of yeast on the lipid metabolism of rats. Bulletin of the Faculty of Home Life Science, Fukuoka Women's University, 16, 65, (1984)). Also disclosed is a case in which the culture supernatant of *Saccharomyces cerebisiae* lowers the serum cholesterol level of mice [Tadaaki Kishida, On the serum Cholesterol-Lowering Effect of *Saccharomyces cerebisiae* Liquid Culture. Jurnal of Japanese Society of Food and Nutrition, 26, 371, (1973)].

However, there is only a few reports in which effect of yeasts other than brewer's yeast or its constituent on improvement of lipid matabolism was demonstrated.

In the human liver, primary bile acids such as cholic acid and chenodeoxycholic acid are synthesized from cholesterol, and conjugated with glycine or taurine, to thereby yield glycine-conjugated or taurine-conjugated bile acid, which are secreted via the bile duct to the digestive tract. Bile acid causes lipid contained in foods and drinks to emulsify and disperse by its surface activation effect, and promotes digestion and absorption of lipid. The bile acid is then actively absorbed again from the ileum, returned to the liver via the portal vein, and resecreted to the digestive tract again. Thus, bile acids repeat enterohepatic circulation.

A portion of bile acid which has not been absorbed by the ileum undergoes modification by enterobacteria; e.g., deconjugation, 7α-dehydroxylation, oxidation, reduction, or epimerization, to thereby convert to secondary bile acid. Predominant secondary bile acids produced through the process are deoxycholic acid and lithocholic acid, which are formed by 7α-dehydroxylation of primary bile acids (cholic acid and chenodeoxycholic acid, respectively. A portion of secondary bile acid is passively absorbed by the large intestine and transferred to the liver, repeating enterohepatic-circulation in similar fashion to the case of primary bile acid. The remaining portion of secondary bile acid is excreted into feces.

In recent years, secondary bile acids such as deoxycholic acid and lithocholic acid produced by enterobacteria existing in the large intestinal tract have been found to be closely related to onset of colorectal cancer, liver cancer, pancreatic cancer, bile duct cancer, etc. In general, the carcinogenesis process is conceived to include an initiation step in which a gene is mutated by a chemical carcinogen, radiation, or a virus, and a promotion step in which abnormality occurs in growth and differentiation through long-term exposure to a promoter. Hitherto, there is disclosed that secondary bile acids such as deoxycholic acid and lithocholic acid act as a promoter in the second step, to thereby promote onset of colorectal cancer, liver cancer, pancreatic cancer, bile duct cancer, etc. (Narisawa, T., et al., *J. Natl. Cancer Inst.*, 53, 1093-1097, 1974; Tsuda, H., et al., *Gann*, 75, 871-5, 1984; and Makino, T., et al., *J. Natl. Cancer Inst.*, 76, 967-75, 1986). There is also disclosed that the carcinogenetic promoter activity of secondary bile acid is considerably stronger than that of primary bile acid (Narisawa, T., et al., *J. Natl. Cancer Inst.*, 53, 1093-1097, 1974; and Reddy, B S., et al., *Cancer Res.*, 37, 3238-3242, 1977). Moreover, there has recently been disclosed that deoxycholic acid may be related to onset of cholelithiasis other than cancers (Marcus, S N., Heaton, K W., *Gut*, 29, 522-533, 1988).

Thus, since secondary bile acids such as deoxycholic acid and lithocholic acid produced by enterobacteria existing in the large intestinal tract have a strong carcinogenetic promoter activity and cause cholelithiasis, diseases such as colorectalcancer, liver cancer, pancreatic cancer, bile duct cancer, and cholelithiasis can be prevented and treated through inhibition of secondary bile acid production.

Hitherto, secondary bile acid production inhibitors have been disclosed, even though the inhibitory effect is weak. These inhibitors are ampicillin—a type of penicillin derivative—(Low-Beer, T S., Nutter, S., *Lancet*, 2(8099), 1063-1065, 1978), 3α,12β-dihydroxy-5β-cholane-24-N-methylamine (Roda, A., et al., *J. Pharm. Sci.*, 81, 237-240, 1992); lactulose—a type of oligosaccharide—(Magengast, F M., *Eur. J. Clin. Invest.*, 18, 56-61, 1988); and wheat bran (Lampe, J W., et al., *Gut*, 34, 531-536, 1993).

Ampicillin and 3α,12β-dihydroxy-5β-cholane-24-N-methylamine inhibit secondary bile acid production by removing bacteria which catalyze 7α-dehydroxylation in the large intestinal tract. However, when these inhibitors are employed for a long period of time, there arise problems such as generation of resistant bacteria and occurrence of adverse side effects. In addition, selective exclusion of bacteria which relates to secondary bile acid production by use of antibiotics is impossible, and use of antibiotics simultaneously excludes enterobacteria which play an important role in maintaining the human health; e.g., *Lactobacillus* and *Bifidobacterium*, and this is greatly problematic.

Lactulose and wheat bran are thought to suppress activity of 7α-dehydroxylase which has optimal pH of a neutral region by lowering pH in the large intestinal track and thereby lower the production of secondary bile acid. However, these substances exert poor effectiveness, which does not reach the level for contributing to prevention and treatment of the diseases.

In view of the foregoing, an object of the present invention is to provide a cholesterol-lowering agent capable of effectively lowering the blood or hepatic cholesterol level by use of a safe yeast causing fewer and less severe side effects.

Another object of the present invention is to provide a secondary bile acid production inhibitor of high effectiveness and safety, useful for preventing and treating diseases such as colorectal cancer, liver cancer, pancreatic cancer, bile duct cancer, and cholelithiasis.

DISCLOSURE OF THE INVENTION

The present inventors have carried out extensive studies, and have found that the yeasts belonging to the following specific groups exert an effect of effectively lowering the blood or hepatic cholesterol and provide fewer and less severe side effects, and that the yeasts exert an effect of inhibiting transformation of primary bile acid to secondary bile acid. The present invention has been accomplished on the basis of these findings.

Accordingly, the present invention provides a cholesterol-lowering agent containing, as an active ingredient, at least one yeast belonging to *Candida, Issatchenkia, Hanseniaspora, Kloeckera, Kluyveromyces, Pichia,* or *Torulaspora,* as well as foods and drinks containing the yeast.

The present invention also provides use of these specific yeasts for producing a cholesterol-lowering agent, as well as foods and drinks for lowering cholesterol.

Further, the present invention provides a treatment method for lowering cholesterol through administration of these specific yeasts.

Still further, the present invention provides a secondary bile acid production inhibitor containing, as an active ingredient, a yeast, as well as foods and drinks containing the yeast.

Yet further, the present invention provides use of the yeast for producing a secondary bile acid production inhibitor, as well as foods and drinks for inhibiting secondary bile acid production.

Still further, the present invention provides a treatment method for inhibiting secondary bile acid production through administration of a yeast.

BEST MODES FOR CARRYING OUT THE INVENTION

Figure 1:
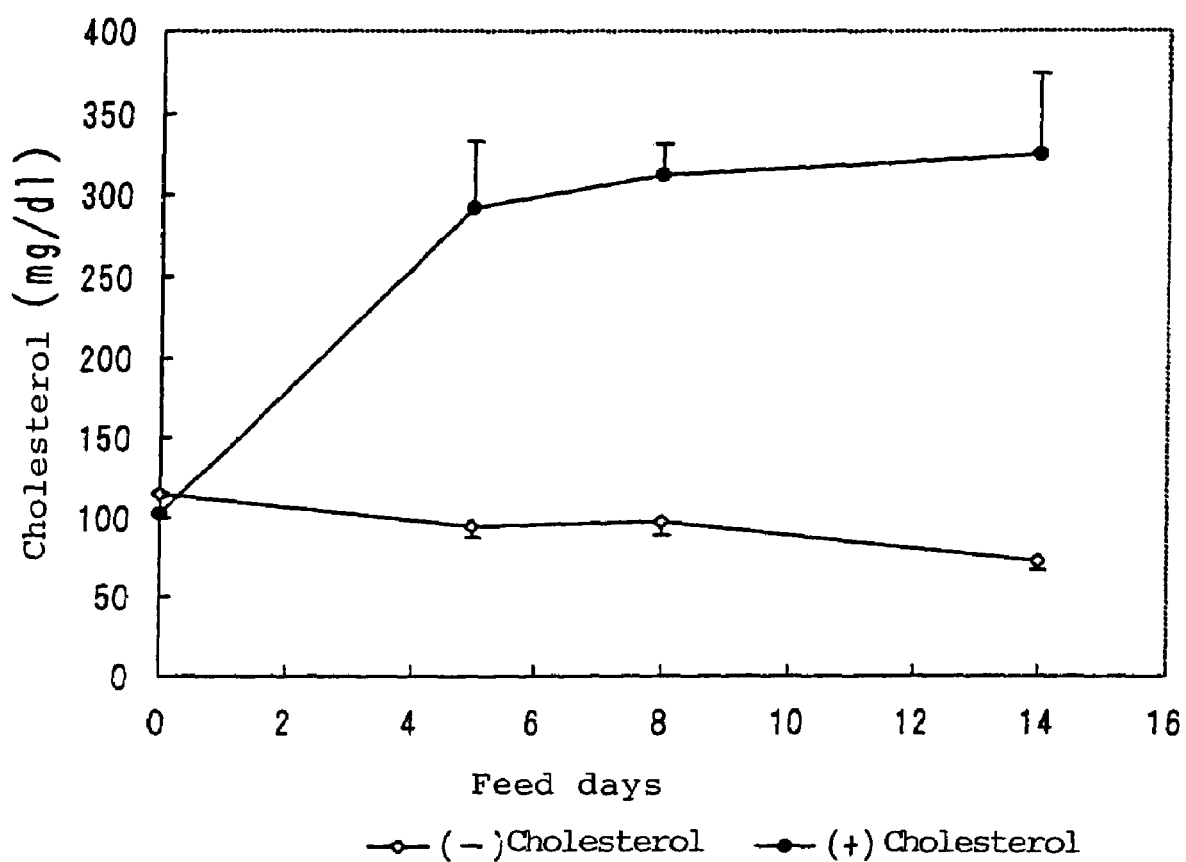
FIG. 1 is a graph showing plasma cholesterol levels of a cholesterol-added diet administration group and a no-cholesterol-added diet administration group.

The yeast to be used in the cholesterol-lowering agent or foods and drinks according to the present invention is a yeast belonging to *Candida, Issatchenkia, Hanseniaspora, Kloeckera, Kluyveromyces, Pichia,* or *Torulaspora.* These yeast may be used singly or in combination of two or more species. The above yeast may be live cells, heated cells, lyophilized products, milled products thereof, or contents thereof.

Examples of preferred yeasts belonging to the above groups include *Candida kefyr, Issatchenkia orientalis, Hanseniaspora uvarum, Kloeckera africana, Kluyveromyces marxianus, Kluyveromyces lactis, Pichia farinosa,* and *Torulaspora delbrueckii.* Of these, most preferred yeasts are the following:

*Candida kefyr* YIT 8237 (FERM BP-7214, original deposit date Jul. 16, 1999; depository organization, Ministry of International Trade and Industry, National Institute of Bioscience and Human-Technology, Agency of Industrial Science and Technology (address: 1-3, Higashi 1-chome, Tsukuba-shi, Ibaraki-ken 305-8566 JAPAN (the same applies hereafter)); *Hanseniaspora uvarum* YIT 8164 (FERM BP-7212, original deposit date Jul. 16, 1999); *Issatchenkia orientalis* YIT 8266 (FERM BP-7215, original deposit date Jul. 16, 1999); *Kloeckera africana* YIT 8165 (FERM BP-7213, original deposit date Jul. 16, 1999), *Kluyveromyces marxianus* YIT 8292 (FERM BP-7217, original deposit date Jul. 16, 1999), *Kluyveromyces lactis* YIT 8263 (FERM BP-7216, original deposit date Jul. 16, 1999), *Pichia farinosa* YIT 8058 (FERM BP-7210, original deposit date Jul. 16, 1999), and *Torulaspora delbrueckii* YIT 8114 (FERM BP-7211, original deposit date Jul. 16, 1999).

From ancient times, these microorganisms have been known to be yeasts for producing foods (wine, milk liquor, cheese), and are strains that are considerably safe to the human body.

The above strains have characteristics as shown in Tables 1 to 5. The properties are nearly the same as those of similar microorganisms disclosed in "The yeast, 3rd edition," (N. J. W. Kreger-Van Rij, Elsevier Science Publishers B. V., Amsterdam, 1984).

TABLE 1 characteristics of Strains

| | Strains | *Candida kefyr* YIT 8237 | *Hanseniaspora uvarum* YIT 8164 | *Issatchenkia orientalis* YIT 8266 | *Kloeckera africana* YIT 8165 | *Kluyveromyces marxianus* YIT 8292 | *Kluyveromyces lactis* YIT 8263 | *Pichia farinosa* YIT 8058 | *Torulaspora delbrueckii* |
|---|---|---|---|---|---|---|---|---|---|
| Fermentation | D-Glucose | + | + | + | + | + | + | + | + |
| | D-Galactose | + | − | − | − | − | + | − | +− |
| | Maltose | − | − | − | − | − | − | − | +− |
| | Me-α-D-glucoside | − | − | − | − | − | − | − | +− |
| | Sucrose | + | − | − | − | − | +− | − | +− |
| | α,α-Trehalose | − | − | − | − | + | − | + | +− |
| | Melibiose | − | − | − | − | − | − | − | +− |
| | Lactose | +− | − | − | − | − | +− | − | − |
| | Cellobiose | − | + | − | − | +− | − | +− | − |
| | Melezitose | − | − | − | − | − | − | − | − |
| | Raffinose | +− | − | − | − | − | +− | − | +− |
| | Inulin | + | − | − | − | − | − | − | +− |
| | Starch | − | − | − | − | − | − | − | − |
| | D-Xylose | − | − | − | − | − | − | − | − |
| Growth | D-Glucose | + | + | + | + | + | + | + | + |
| | D-Galactose | + | − | +− | − | + | + | + | + |
| | D-Sorbose | − | − | − | − | +− | + | +− | +− |
| | D-Glucosamine | − | − | − | − | − | − | − | +− |
| | D-Ribose | +− | − | − | − | +− | − | + | − |

TABLE 2

| | Strains | *Candida kefyr* YIT 8237 | *Hanseniaspora uvarum* YIT 8164 | *Issatchenkia orientalis* YIT 8266 | *Kloechera africana* YIT 8165 | *Kluyveromyces marxianus* YIT 8292 | *Kluyveromyces lactis* YIT 8263 | *Pichia farinosa* YIT 8058 | *Torulaspora delbrueckii* YIT 8114 |
|---|---|---|---|---|---|---|---|---|---|
| Growth | D-Xylose | +− | − | − | − | +− | − | +− | − |
| | L-Arabinose | +− | − | − | − | − | − | − | − |
| | D-Arabinose | − | − | − | − | − | − | − | − |
| | L-Rhamnose | − | − | − | − | +− | − | +− | − |
| | Sucrose | + | − | + | +− | + | + | + | +− |
| | Maltose | − | − | − | + | − | + | − | +− |
| | α,α-Trehalose | +− | − | − | − | +− | + | +− | + |
| | Me-α-D-glucoside | − | − | − | − | − | + | − | +− |
| | Cellobiose | +− | + | − | + | +− | + | +− | − |
| | Salicin | +− | − | − | − | +− | + | +− | − |
| | Arbutin | − | + | − | − | +− | + | +− | − |
| | Melibiose | − | − | − | − | − | − | − | +− |
| | Lactose | + | − | +− | − | + | + | + | − |
| | Raffinose | + | − | − | − | − | + | − | +− |
| | Melezitose | − | − | − | − | − | + | − | +− |
| | Inulin | − | − | − | − | − | − | − | +− |
| | Starch | − | − | − | − | − | − | − | − |
| | Glycerol | +− | − | + | − | + | + | + | +− |
| | Erythritol | − | − | − | − | + | − | + | − |
| | Ribitol | − | − | − | − | + | − | + | − |
| | Xylitol | − | − | − | − | + | + | + | +− |

TABLE 3

|  | Strains | *Candida kefyr* YIT 8237 | *Hanseniaspora uvarum* YIT 8164 | *Issatchenkia orientalis* YIT 8266 | *Kloechera africana* YIT 8165 | *Kluyveromyces marxianus* YIT 8292 | *Kluyveromyces lactis* YIT 8263 | *Pichia farinosa* YIT 8058 | *Torulaspora delbrueckii* YIT 8114 |
|---|---|---|---|---|---|---|---|---|---|
| Growth | L-Arabinitol |  | − | − |  | − | − | − | − |
|  | D-Glucitol | +− | +− | − |  | + | + | + | − |
|  | D-Mannitol | +− | +− | − | − | + | + | + | +− |
|  | Galactitol | − | − | − |  | − | − | − | − |
|  | myo-Inositol |  | − | − |  | − | − | − | − |
|  | D-Glucono-1,5-Lactone |  | + | − |  | + | − | + | +− |
|  | 2-Keto-D-gluconate |  | + | − | − | +− | − | +− | + |
|  | D-Gluconate |  | − | − |  | + | − | + | − |
|  | D-Glucronate |  | − | − |  | − | − | − | − |
|  | D-Galacturonate |  | − | − |  | + | − | − | − |
|  | DL-Lactate | + | − | + |  | − | + | − | +− |
|  | Succinate | +− | − | + | − | +− | + | +− | − |
|  | Citrate | +− | − | +− | − | + | +− | + | − |
|  | Methanol | − | − |  |  | − | − | − | − |
|  | Ethanol | − | + |  |  | + | + | + | + |
|  | Propane-1,2-diol | − | − | − |  | − | − | − | − |
|  | Butane-2,3-diol | − | − | − |  | + | − | − | − |
|  | Nitrate | − | − | − |  | − | − | − | − |
|  | Nitrite | − | − | − |  | − | − | − | +− |
|  | Ethylamine |  | + | + |  | + | + | + | +− |
|  | L-Lysine |  | + | + |  | + | + | +− | + |

TABLE 4

|  | Strains | *Candida kefyr* YIT 8237 | *Hanseniaspora uvarum* YIT 8164 | *Issatchenkia orientalis* YIT 8266 | *Kloechera africana* YIT 8165 | *Kluyveromyces marxianus* YIT 8292 | *Kluyveromyces lactis* YIT 8263 | *Pichia farinosa* YIT 8058 | *Torulaspora delbrueckii* YIT 8114 |
|---|---|---|---|---|---|---|---|---|---|
| GrowTh | Cadaverine |  | + | + |  | + | + | + | − |
|  | Creatine |  | − | − |  | − | − | − | − |
|  | Creatinine |  | − | − |  | − | − | − | − |
|  | Glucosamine |  | − | − |  | − | − | − | − |
|  | Imidazole |  | − | − |  | − | − | − | − |
|  | W/O Vitamins |  | − | + |  | +− | − | +− | +− |
|  | W/O myo-Inositol |  | − | + |  | + | + | + | + |
|  | W/O Pantothenic acid |  | − | + |  | + | + | + | + |
|  | W/O Biotin |  | +− | + |  | + | +− | + | +− |
|  | W/O Thiamine |  | +− | + |  | +− | + | +− | + |
|  | W/O Biotin & Thiamine |  | − | + |  | +− | +− | +− | +− |
|  | W/O Pyridoxine |  | − | + |  | + | + | + | + |
|  | W/O Pyridoxine & Thiamine |  | − | + |  | +− | +− | +− | +− |
|  | W/O Niacin |  | − | + |  | + | − | + | + |
|  | W/O PABA |  | + | + |  | + | + | + | + |
|  | 25° C. | + | + | + |  | + | + | + | + |
|  | 30° C. | + | + | + |  | + | + | + | + |
|  | 35° C. | + | − | + | + | + | + | + | +− |
|  | 37° C. | + | − | + | − | + | + | + | +− |
|  | 40° C. | + | − | + |  | + | − | + | − |
|  | 0.01% Cycloheximide |  | + | − |  | − | + | − | − |

TABLE 5

|  | Strains | *Candida kefyr* YIT 8237 | *Hanseniaspora uvarum* YIT 8164 | *Issatchenkia orientalis* YIT 8266 | *Kloechera africana* YIT 8165 | *Kluyveromyces marxianus* YIT 8292 | *Kluyveromyces lactis* YIT 8263 | *Pichia farinosa* YIT 8058 | *Torulaspora delbrueckii* YIT 8114 |
|---|---|---|---|---|---|---|---|---|---|
| Growth | 0.1% Cycloheximide |  | + | − | − | − | + | − | − |
|  | 1% Acetic |  | − | − |  | − | − | − | − |
|  | 50% D-Glucose |  | +− | − | + | + | − | + | + |
|  | 60% D-Glucose |  | − | − |  | + | − | + | +− |
| Additional | Starch | − | − | − |  |  |  |  |  |

TABLE 5-continued

| | Strains | Candida kefyr YIT 8237 | Hanseniaspora uvarum YIT 8164 | Issatchenkia orientalis YIT 8266 | Kloechera africana YIT 8165 | Kluyveromyces marxianus YIT 8292 | Kluyveromyces lactis YIT 8263 | Pichia farinosa YIT 8058 | Torulaspora delbrueckii YIT 8114 |
|---|---|---|---|---|---|---|---|---|---|
| Character- istics | production Acetic acid production | − | − | − | | − | − | − | − |
| | Urea hydrolysis | − | − | − | | − | − | − | − |
| | Diazonium Blue B reaction | − | − | − | | − | − | − | − |

The yeasts which are used in the secondary bile acid production inhibitor of the present invention will next be described.

No particular limitation is imposed on the yeasts which are used in the secondary bile acid production inhibitor. The yeasts include live cells produced by culturing the yeasts, heated cells, lyophilized products, milled products thereof, and contents thereof.

The yeast to be used in the present invention has never been reported to inhibit elimination of the 7α-hydroxyl group of cholic acid or similar substances, to thereby inhibit formation of secondary bile acid such as deoxycholic acid. Since the present invention employs the effect of yeast on suppression and inhibition of transformation of primary bile acid to secondary bile acid, yeasts which have excellent absorption power to primary bile acids, such as, particularly, cholic acid, taurocholic acid, glycocholic acid, and chenodeoxycholic acid, as well as excellent power to elevate the intestinal concentration level of short-chain fatty acids such as acetic acid, propionic acid, and butyric acid are preferred, from the viewpoint of excellent effect of inhibiting 7α-dehydroxylation.

Examples of yeasts preferably used in the secondary bile acid production inhibitor include *Issatchenkia*, *Kluyveromyces*, *Hanseniaspora*, *Saccharomyces*, *Hyphopichia*, *Candida*, *Torulaspora*, *Pichia*, and *Zygosaccharomyces*. These yeasts may be used singly or in combination of two or more species.

Specific examples include *Issatchenkia orientalis*, *Kluyveromyces marxianus*, *Kluyveromyces lactis*, *Kluyveromyces thermotolerans*, *Hanseniaspora uvarum*, *Saccharomyces cerevisiae*, *Saccharomyces dairensis*, *Saccharomyces exiguus*, *Saccharomyces unisporus*, *Saccharomyces bayanus*, *Hyphopichia burtonii*, *Candida kefyr*, *Candida etchellsii*, *Candida zeylanoides*, *Candida solani*, *Candida maltosa*, *Candida tropicalis*, *Candida cylindracea*, *Candida utilis*, *Torulaspora delbrueckii*, *Pichia anomala*, *Pichia holstii*, and *Zygosaccharomyces rouxii*. Of these, most preferred yeasts are the following:

*Issatchenkia orentalis* YIT 8266 (FERM BP-7215); *Kluyveromiyces marxianus* YIT 8292 (FERM BP-7217); *Kluyveromiyces lactis* YIT 8263 (FERM BP-7216); *Kluyveromyces thermotolerans* YIT 8294 (ATCC 20309); *Hanseniaspora uvarum* YIT 8164 (FERM BP-7212); *Saccharomyces cerevisiae* YIT 8116 (ATCC 48554); *Saccharomyces dairensis* YIT 8191 (CBS 3007); *Saccharomyces exiguus* YIT 8109 (CBS 3019); *Saccharomyces unisporus* YIT 8226 (FERM BP-7209, original deposit date; Mar. 25, 1999, depository organization, Ministry of International Trade and Industry, National Institute of Bioscience and Human-Technology, Agency of Industrial Science and Technology (address: 1-3, Higashi 1-chome, Tsukuba-shi, Ibaraki-ken 305-8566 JAPAN); *Saccharomyces bayanus* YIT 8128 (CBS 380); *Hyphopichia burtonii* YIT 8299 (CBS 2352); *Candida kefyr* YIT 8237 (FERM BP-7214); *Candida etchellsii* YIT 8278 (ATCC 60119); *Candida zeylanoides* YIT 8018 (IFO 0719); *Candida solani* YIT 8023 (CBS 1908); *Candida maltosa* YIT 8283 (ATCC 28140); *Candida tropicalis* YIT 8286 (CBS 94); *Candida cylindracea* YIT 8276 (ATCC 14830); *Candida utilis* YIT 8204 (ATCC 9950); *Torulaspora delbrueckii* YIT 8313 (JCM 2204) and YIT 8133 (IFO 1172); *Pichia anomala* YIT 8298 (JCM 3587) and YIT 8297 (JCM 3583); *Pichia holstii* YIT 8038 (ATCC 58048); and *Zygosaccharomyces rouxii* YIT 8129 (CBS 732).

From ancient times, these yeasts have been used to produce foods (wine, cheese), and are considerably safe microorganisms to the human body. The cells thereof, which are particles having a particle size of some microns, are much easily taken as compared with particles having a size of 20 μm or more, which provide unfavorable sensation when taken. The above yeasts; e g., *Issatchenkia orentalis* YIT 8266 (FERM BP-7215), have specific characteristics as shown in Table 6. The characteristics are nearly the same as those of similar yeasts disclosed in "The yeast, 3rd edition," (N. J. W. Kreger-Van Rij, Elsevier Science Publishers B. V., Amsterdam, 1984).

TABLE 6

Characteristics of *Issatchenkia orentalis* YIT 8266

| Fermentation | |
|---|---|
| D-Glucose | + |
| D-Galactose | − |
| Maltose | − |
| Me-α-D-glucose | − |
| Sucrose | − |
| α,α-Trehalose | − |
| Melibiose | − |
| Lactose | − |
| Cellobiose | − |
| Melezitose | − |
| Raffinose | − |
| Inulin | − |
| Starch | − |
| D-Xylose | − |
| Growth | |
| D-Glucose | + |
| D-Galactose | +− |
| L-Sorbose | − |
| D-Glucosamine | − |
| D-Ribose | − |
| D-Xylose | − |
| L-Arabinose | − |
| D-Arabinose | − |
| L-Rhamnose | − |
| Sucrose | − |
| Maltose | − |
| α,α-Trehalose | − |
| Me-α-D-glucoside | − |
| Cellobiose | − |
| Salcin | − |

TABLE 6-continued

Characteristics of *Issatchenkia orentalis* YIT 8266

| | |
|---|---|
| Arbutin | − |
| Melibiose | − |
| Lactose | + |
| Raffinose | − |
| Melezitose | − |
| Inulin | − |
| Starch | − |
| Glycerol | + |
| Erythritol | − |
| Ribitol | − |
| Xylitol | − |
| L-Arabinitol | − |
| D-Glucitol | − |
| D-Mannitol | − |
| Galactitol | − |
| myo-Inositol | − |
| D-Glucono-1,5-lactone | − |
| 2-Keto-D-gluconate | − |
| D-Gluconate | − |
| D-Glucuronate | − |
| D-Galacturonate | − |
| DL-Lactate | + |
| Succinate | + |
| Citrate | + |
| Methanol | − |
| Ethanol | + |
| Propane-1,2-diol | − |
| Butane-2,3-diol | − |
| Nitrate | − |
| Nitrite | − |
| Ethylamine | + |
| L-Lysine | + |
| Cadaverine | + |
| Creatine | − |
| Creatinine | − |
| Glucosamine | − |
| Imidazole | − |
| W/O Vitamin | + |
| W/O myo-Inositol | + |
| W/O Pantothenic acid | + |
| W/O Biotin | + |
| W/O Thiamin | + |
| W/O Biotin & thiamin | + |
| W/O Pyridoxine | + |
| W/O Pyridoxine & thiamin | + |
| W/O Niacin | + |
| W/O PABA | + |
| 25° C. | + |
| 30° C. | + |
| 35° C. | + |
| 37° C. | + |
| 40° C. | + |
| 0.01% Cycloheximide | − |
| 0.1% Cycloheximide | − |
| 1% Acetic acid | − |
| 50% D-Glucose | − |
| 60% D-Glucose | − |
| Additional characteristics | |
| Starch production | − |
| Acetic acid production | − |
| Urea hydrolysis | − |
| Diazonium Blue B reaction | − |

The yeast of the present invention can be produced through a routine method; e.g., culturing in a complex medium containing yeast extract and polypeptone or in a synthetic medium predominantly containing an inorganic salt.

The thus-produced yeast can be employed, in the forms of live cells, lyophilized products thereof, killed cells obtained through heating or similar treatment, milled products thereof, or contents thereof, in a pharmaceutical composition or foods and drinks. In addition, commercially available yeast may also be used.

The aforementioned yeast may be formed into a pharmaceutical composition of a variety of drug foams, through a routine method together with pharmaceutically acceptable carriers. When a solid drug for peroral administration is prepared, the aforementioned yeast is mixed with a vehicle and optional additives such as a binder, a disintegrant, a lubricant, a colorant, a flavoring agent, and an aroma, and the resultant mixture is formed, through a customary method, into tablets, coated tablets, granules, powder, or capsules. Additives generally employed in the art may be used as the above additives. Examples include vehicles such as lactose, white sugar, sodium chloride, glucose, starch, calcium carbonate, kaolin, microcrystalline cellulose, and silicic acid;, binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, calcium phosphate, and poly(vinylpyrrolidone); disintegrants such as dry starch, sodium alginate, powdered agar, sodium hydrogencarbonate, calcium carbonate, sodium lauryl sulfate, stearic monoglyceride, and lactose; lubricants such as purified talc, stearate salts, borax, and polyethylene glycol; and flavoring agents such as white sugar, orange peel, citric acid, and tartaric acid.

When a liquid drug for peroral administration is prepared, the aforementioned yeast is mixed with additives such as a flavoring agent, a buffer, a stabilizer, and an aroma, and the resultant mixture is formed, through a customary method, into peroral liquid, syrups, and elixirs. The aforementioned flavoring agents may also be used. Examples of the buffer include sodium citrate, and examples of the stabilizer include tragacanth, gum arabic, and gelatin.

The foods and drinks of the present invention can be produced by adding the aforementioned yeast to a variety of foods and drinks. Examples of preferred foods and drinks include fermented milk, fruit-juice-blended drinks, soup, rice cakes, and cookies. Animals feeds are also included in the foods and drinks.

The amount of yeast which is to be added to the aforementioned drug varies in accordance with the drug form and the condition of the patient to which the drug is to be administered. Generally, an amount of 1-100 wt. % in the drug is preferred. The daily dose of the aforementioned drug or foods and drinks varies in accordance with the condition, body weight, age, sex, etc. of the patient, and cannot be determined as a fixed value. Generally, the daily dose per adult is approximately 10 mg to 30 g based on yeast, preferably approximately 1-5 g. The yeast is administered preferably once per day or 2-4 times per day in a divided manner.

EXAMPLES

The present invention will next be described in more detail by way of examples, which should not be construed as limiting the invention thereto. As used herein, "%" refers to "wt. %."

Example 1

(A) Preparation of Yeasts

Each of a variety of yeasts, which had been stored in a potato dextrose agar slant medium, was inoculated for one platinum loop into a medium (100 mL) shown in Table 7 placed in a Sakaguchi flask (500 mL), and the medium was subjected to shaking culture (120 spm) at 30° C.

Two days after initiation of culture, the culture (amount corresponding to two Sakaguchi flasks) was inoculated into a 10-liter fermentation tank (effective volume 7 L), and aerobic agitation culture was carried out at 3.0° C. for two days, under the following conditions: aeration rate of 0.5 vvm, rotation rate of 250 rpm, and pH of 6.0 (automatically controlled by 5N sodium hydroxide).

After completion of culturing, the supernatant and cells were separated by means of a cooling centrifugator, and the separated cells were washed twice by distilled water. The washed cells were placed in a 2-L Erlenmeyer flask, and distilled water (1 L) was added thereto. The mixture was heated at 115° C. for 10 minutes in an autoclave. The thus-heated cells as such were lyophilized.

TABLE 7

Composition of Medium for Pre-Culture and Culture

| | |
|---|---|
| Glucose (Kanto Chemical) | 30 g |
| Polypeptone (Daigo Eiyo) | 10 g |
| Yeast extract (Daigo Eiyo) | 5 g |
| Monopotassium phosphate (Wako Pure Chemical) | 1 g |
| Dipotassium phosphate (Wako Pure Chemical) | 2 g |
| Magnesium sulfate (Wako Pure Chemical) | 0.5 g |
| Tap water | 1 L |
| pH 6.0 | |

(B) Preparation of Test Diets

By use of the yeast produced in (A), ingredients were mixed in a routine manner, to thereby prepare diets having a composition shown in Table 8. Each diet contains cholesterol; i.e., cholesterol (0.5%) and sodium cholate (0.25%). In order to prepare a yeast-containing diet, each type of lyophilized yeast cells was added in an amount of 5% or 10%.

TABLE 8

Diet Composition (%)

| Ingredients | Control group | 10% Yeast administration group | 5% Yeast administration group |
|---|---|---|---|
| Casein | 22.30 | 17.35 | 19.83 |
| Soybean oil | 1.0 | 1.0 | 1.0 |
| Lard | 10.0 | 9.45 | 9.72 |
| Inorganic salt | 4.0 | 3.54 | 3.77 |
| Vitamins | 1.0 | 1.0 | 1.0 |
| Choline bitartrate | 0.15 | 0.15 | 0.15 |
| Cholesterol | 0.5 | 0.5 | 0.5 |
| Sodium cholate | 0.25 | 0.25 | 0.25 |
| Filter paper powder | 10.0 | 7.46 | 8.73 |
| Sucrose | 50.80 | 50.12 | 50.46 |
| Yeast cells | 0.0 | 10.0 | 5.0 |

Test method Cholesterol-lowering Effect (1) Test Diet

Test diets prepared in Example 1(B) were employed.

(2) Animal and Breeding Method a) Group of Animals Administered 10% Yeast-containing Diet Male, 5-week-old Wistar rats (obtained from Clea Japan) had been pre-bred for 7 days with diet powder F-2 (product of Oriental Yeast). The rats were divided into groups, each group containing 8 rats. To each group, the 10% yeast-containing diet shown in Table 8 was administered for 7 days. The rats were bred in group in a metal-made cage, and allowed to consume the administered diet and water ad libitum.

b) Group of Animals Administered 5% Yeast-containing Diet

Male, 5-week-old Wistar rats (obtained from Nihon Kurea) had been pre-bred for 7 days with diet powder F-2 (product of Oriental Yeast). The rats were divided into groups, each group containing 8 rats. To each group, the 5% yeast-containing diet shown in Table 8 was administered for 14 days. The rats were bred individually in a metal-made cage, and the amount of administered diet was limited to 15 g/day, but water was provided ad libitum.

(3) Measurement of Plasma Lipids a) Group of Animals Administered 10% Yeast-containing Diet Seven days after initiation of administration, blood was collected, under anesthetization with Nembutal (without fasting), from the abdominal aorta of each rat by use of a cannula, and the plasma cholesterol concentration and the plasma HDL concentration were measured. The total cholesterol concentration was measured by means of a biochemical automatic analyzer (Model 7170, Hitachi).

The HDL cholesterol concentration was measured by means of a biochemical automatic analyzer (Model 7170, Hitachi), after lipoprotein components other than HDL had been precipitated by use of Determiner HDL (product of Kyowa Medics).

b) Group of Animals Administered 5% Yeast-containing Diet

Seven days after initiation of administration, blood was collected from the tail vein of each rat, and the plasma cholesterol concentration and the plasma HDL concentration were measured. The total cholesterol concentration was measured by means of a biochemical automatic analyzer (Model 7170, Hitachi).

The HDL cholesterol concentration was measured by means of a biochemical automatic analyzer (Model 7170, Hitachi), after lipoprotein components other than HDL had been precipitated by use of Determiner HDL (product of Kyowa Medics).

(4) Measurement of Intrahepatic Lipids

After perfusion of the liver by use of physiological saline, the liver was collected and lyophilized. Lipid extraction was performed by use of chloroform:methanol (2:1) in accordance with the method of Folch et al. The resultant chloroform lower layer was concentrated to solid, and the solid was diluted again by use of ethanol. The diluted sample was subjected to measurement of lipid components contained in the liver. Among hepatic lipids, the amount of cholesterol was measured by use of Determiner TC 555.

Method for Evaluating Animal Test Results (1) Statistical Method

Upon statistical analysis of the animal test results, homogeneity of variance was tested by the Bartlett method. When the variance was found to be homoscedastic, analysis of variance was performed in a one-way layout manner, followed by Dunnett's multiple comparison test, whereas when the variance was found to be heteroscedastic (test objects from which significant difference was obtained through Bartlett test at a level of significance under 5%), analysis of variance was performed through the Kruskal-Wallis test, followed by Dunnett's multiple comparison test. In Dunnett's multiple comparison test, the level of significance was set at 5% and 1%, and the test was performed at each level of significance.

(2) Method for Obtaining Percent Reduction of Lipid Components

<Percent Reduction in Plasma Cholesterol>

The expression "100% reduction in plasma cholesterol" refers to a plasma cholesterol level lowered to a plasma cholesterol level of a rat belonging to a group administered an ordinary diet (no-cholesterol-added). The express "0% reduction in plasma cholesterol" refers to a plasma cholesterol level elevated to a plasma cholesterol level of a rat belonging to a group administered a cholesterol-added diet (control).

(3) Atherogenic Index

Atherogenic index (AI) is represented by the following formula:

$$AI = (VLDL\ cholesterol + LDL\ cholesterol)/HDL\ cholesterol.$$

AI was calculated from the total plasma cholesterol level and the plasma HDL cholesterol; i.e., actual plasma lipid measurements, according to the following formula:

$$AI = ((total\ plasma\ cholesterol) - (plasma\ HDL\ cholesterol))/(plasma\ HDL\ cholesterol).$$

The percent improvement of atherogenic index was calculated from the AI value of each yeast-containing-diet administration group and the AI value of cholesterol-added-diet administration group (control group). The "expression 100% improvement of atherosclerotic index" refers to an AI value identical to the AI value of the no-cholesterol-added-diet administration group. The expression "0% improvement of atherosclerotic index" refers to an AI value identical to the AI value of the cholesterol-added-diet administration group (control group).

(4) Body Weight Measurement

The body weight of each rat was measured upon purchase thereof. The rats were separated into groups such that no significant difference in body weight was present among the groups, and pre-breeding was started. The body weight was measured before starting the test and after completion of the test.

The aforementioned test method was adopted to the following pre-tests and Examples.

Preliminary Test:

Blood was collected from the tail vein of rats after administration of the cholesterol-added diet; i.e., on day 0, day 5, and day 8. On day 14, blood was collected, under anesthetization with Nembutal, from the abdominal aorta. Plasma was separated from each collected blood sample, and subjected to lipid component measurement through an enzyme method.

As shown in FIG. 1, the plasma cholesterol level of the cholesterol-added diet administration group increased to approximately the maximum at day 5. Thereafter, a slight increase was observed until day 14, but no significant change was observed. The plasma cholesterol level of the no-cholesterol-added diet administration group (diet prepared by removing cholesterol and sodium cholate from the cholesterol-added diet) did not increase during the test period, and a tendency of slight decrease in level was observed.

Table 9 shows the plasma lipid concentration on day 14 after initiation of administration of cholesterol-added diet. The cholesterol level of the no-cholesterol-added diet administration group is 72.5 mg/dL, whereas that of the cholesterol-added diet administration group is 325.3 mg/dL, indicating an approximately 4.5 fold increase in level. In contrast, the plasma HDL cholesterol level of the cholesterol-added diet administration group is 45.9 mg/dL, significantly lower than that of the no-cholesterol-added diet administration group (31.4 mg/dL).

TABLE 9

| | Plasma Lipid Concentration (day 14) | |
|---|---|---|
| Diet administration groups | Cholesterol (mg/dL) | HDL cholesterol (mg/dL) |
| Cholesterol free diet (Control group) | 72.5 ± 6.1 | 45.9 ± 4.2 |
| Cholesterol added diet (high-fat diet administration group) | 325.3 ± 48.6** | 31.4 ± 4.00** |

**$p < 0.01$

Table 10 shows the hepatic lipid content on day 14 after initiation of administration of the cholesterol-added diet. The cholesterol level of the cholesterol-added diet administration group is about 20 times the cholesterol level of the no-cholesterol-added diet administration group.

TABLE 10

| Intrahepatic Lipid Content (day 14) | |
|---|---|
| Diet administration groups | Total cholesterol (mg/liver) |
| Cholesterol free diet (Control group) | 32.9 ± 8.4 |
| Cholesterol added diet (high-fat diet administration group) | 637.9 ± 60.70** |

**$p < 0.01$

Example 2

Jar culture was performed in accordance with the method of Example 1, to thereby prepare 200 g of lyophilized cells (heated at 110° C. for 10 minutes) of each yeast. Each cell sample was mixed into a cholesterol-added diet at 10% (10% yeast group in Table 8). The resultant diet was administered to each group consisting of eight rats, and consumed ad libitum for seven days.

Tables 11 to 13 show the percent reduction of cholesterol level and the percent improvement (%) of atherosclerotic index, based on the plasma cholesterol level of the high-cholesterol-diet administration control group. No significant change in weight was observed among the tested groups.

TABLE 11

Percent Reduction of Plasma Cholesterol and Percent Improvement of AI

| YIT No. | Yeast taxonomic genus and species | Plasma lipid Percent reduction of cholesterol | Dunnett's test (p<) | Percent improvement of AI (%) | Av. body weight (g) |
|---|---|---|---|---|---|
| 8164 | *Hanseniaspora uvarum* | 76.5 | 0.01 | 78.0 | 224.0 |
| 8301 | *Pichia guilliermondii* | 74.7 | 0.01 | 60.1 | 216.4 |
| 8263 | *Kluyveromyces lactis* | 72.8 | 0.01 | 68.8 | 220.4 |
| 8292 | *Kluyveromyces marxianus* | 65.5 | 0.01 | 55.8 | 219.6 |
| 8266 | *Issatchenkia orientalis* | 64.2 | 0.01 | 55.3 | 225.0 |
| 8299 | *Hyphopichia burtonii* | 62.7 | 0.01 | 54.0 | 219.0 |
| 8058 | *Pichia farinosa* | 60.3 | 0.05 | 51.8 | 212.1 |
| 8237 | *Candida kefyr* | 60.0 | 0.01 | 59.3 | 216.4 |
| 8165 | *Kloeckera africana* | 54.9 | n.s. | 54.1 | 216.8 |
| 8313 | *Torulaspora delbrueckii* | 52.7 | 0.01 | 51.0 | 221.4 |
| 8114 | *Torulaspora delbrueckii* | 52.5 | 0.05 | 46.2 | 217.4 |
| 8298 | *Pichia anomala* | 50.7 | 0.05 | 38.0 | 223.2 |
| 8280 | *Candida glabrata* | 48.1 | 0.05 | 42.9 | 215.0 |
| 8104 | *Kluyveromyces marxianus* | 48.0 | 0.05 | 44.9 | 221.0 |
| 8278 | *Candida etchellsii* | 46.1 | 0.01 | 41.5 | 224.2 |
| 8026 | *Debaryomyces hansenii* | 44.5 | 0.05 | 30.8 | 217.0 |
| 8018 | *Candida zeylanoides* | 43.5 | 0.05 | 48.4 | 218.4 |
| 8007 | *Candida krusei* | 38.3 | 0.05 | 43.8 | 225.6 |
| 8223 | *Candida gropengiesseri* | 38.1 | n.s. | 37.2 | 220.0 |

TABLE 12

Percent Reduction of Plasma Cholesterol and Percent Improvement of AI

| YIT No. | Yeast taxonomic genus and species | Plasma lipid Percent reductin of cholesterol | Dunnett's test | Percent improvement of AI (%) | Av. body weight (g) |
|---|---|---|---|---|---|
| 8247 | *Pichia capsulata* | 38.1 | n.s. | 22.6 | 220.5 |
| 8294 | *Kluyveromyces thermotolerans* | 37.7 | n.s. | 63.4 | 220.4 |
| 8159 | *Candida magnoliae* | 37.1 | n.s. | 51.8 | 220.6 |
| 8281 | *Candida gropengiesseri* | 36.5 | 0.05 | 34.6 | 224.0 |
| 8006 | *Candida parapsilosis* | 36.4 | n.s. | 33.8 | 218.0 |
| 8314 | *Yarrowia lipolytica* | 35.8 | n.s. | 24.5 | 208.2 |
| 8110 | *Torulaspora delbrueckii* | 34.5 | n.s. | 23.5 | 217.0 |
| 8133 | *Torulaspora delbrueckii* | 33.7 | n.s. | 32.3 | 209.8 |
| 8300 | *Pichia etchellsii* | 33.3 | n.s. | 52.0 | 223.2 |
| 8302 | *Pichia membranaefaciens* | 31.5 | n.s. | 46.6 | 220.4 |
| 8241 | *Candida valida* | 30.4 | n.s. | 34.0 | 223.2 |
| 8303 | *Pichia subpelliculosa* | 27.7 | n.s. | 48.2 | 221.4 |
| 8285 | *Candida stellata* | 26.8 | n.s. | 21.3 | 219.0 |
| 8277 | *Candida diversa* | 26.0 | n.s. | 28.6 | 226.4 |
| 8291 | *Issatchenkia terricola* | 25.2 | n.s. | 30.1 | 212.2 |
| 8107 | *Torulaspora delbrueckii* | 24.8 | n.s. | 20.2 | 207.8 |
| 8034 | *Williopsis californica* | 23.2 | n.s. | 10.2 | 214.8 |
| 8023 | *Candida solani* | 22.9 | n.s. | 25.0 | 226.6 |
| 8288 | *Candida vini* | 21.8 | n.s. | 20.7 | 223.8 |
| 8033 | *Pichia anomala* | 20.4 | n.s. | 23.0 | 220.6 |

TABLE 13

Percent Reduction of Plasma Cholesterol and Percent Improvement of AI

| YIT No. | Yeast taxonomic genus and species | Plasma lipid | | | Av. body weight (g) |
|---|---|---|---|---|---|
| | | Percent reduction of cholesterol (%) | Dunnett's test (p<) | Percent improvement of AI (%) | |
| 8012 | *Yarrowia lipolytica* | 13.3 | n.s. | 22.4 | 216.6 |
| 8181 | *Rhodotorula minuta* | 12.2 | n.s. | −15.4 | 224.0 |
| 8304 | *Rhodotorula glutinis* | 1.0 | n.s. | −13.4 | 221.0 |
| 8312 | *Saccharomycopsis malanga* | −2.1 | n.s. | −11.1 | 215.6 |
| 8120 | *Pachytichospora transvaalensis* | −9.7 | n.s. | −24.3 | 207.8 |
| 8317 | *Zygosaccharomyces rouxii* | −10.2 | n.s. | 0.6 | 216.8 |
| 8129 | *Zygosaccharomyces rouxii* | −34.2 | n.s. | −55.9 | 199.2 |
| 8315 | *Zygosaccharomyces bailii* | −67.5 | n.s. | −77.9 | 209.0 |

Example 3

10% Yeast-added Diet Administration Test

Test Method;

Jar culture was performed in accordance with the method of Example 1(A), to thereby prepare 200 g of lyophilized cells of each yeast. Each cell sample was mixed into a cholesterol-added diet at 10% (10% yeast group in Table 8). The resultant diet was administered to each group consisting of eight rats, and consumed ad libitum for seven days. Table 14 shows the results of plasma lipid measurement.

*farinosa* YIT 8058, exhibited remarkably excellent percent reduction of plasma cholesterol and were found to improve atherogenic index.

Example 4

5% Yeast-added Diet Administration Test

The procedure of Example 3 employing male 5-week-old Wistar rats was repeated, except that each lyophilized cell sample was mixed into a diet for test groups at 5% (5% yeast

TABLE 14

Plasma lipid (10% mixed administration)

| Strains | Total cholesterol (mg/dL) | HDL cholesterol (mg/dL) | Reduction of cholesterol (%) | AI (−) | Percent improvement of AI (%) |
|---|---|---|---|---|---|
| Control group (high-fat-diet administration group) | 226.0 ± 14.9 | 21.7 ± 3.4 | — | 9.62 ± 1.75 | — |
| *Kluyveromyces marxianus* YIT 8292 | 134.5 ± 29.7** | 23.2 ± 3.9 | 65.5 | 4.84 ± 1.22** | 55.8 |
| *Issatchenkia orientalis* YIT 8266 | 136.2 ± 18.7** | 23.4 ± 3.0 | 64.2 | 4.88 ± 0.99** | 55.3 |
| Control group (high-fat diet administration group) | 244.5 ± 50.3 | 23.7 ± 3.4 | — | 9.43 ± 2.33 | — |
| *Kluyveromyces lactis* YIT 8263 | 126.8 ± 26.4** | 27.2 ± 1.8 | 72.8 | 3.67 ± 1.06** | 68.8 |
| Control group (high-fat diet administration group) | 230.1 ± 26.9 | 25.9 ± 3.5 | — | 7.97 ± 1.17 | — |
| *Hanseniaspora uvarum* YIT 8164 | 127.5 ± 19.4** | 35.9 ± 4.6** | 76.5 | 2.58 ± 0.54** | 78.0 |
| *Candida kefyr* YIT 8237 | 133.8 ± 19.4** | 27.8 ± 2.4 | 60.0 | 3.87 ± 1.06** | 59.3 |
| Control group (high-fat diet administration group) | 222.0 ± 14.9 | 23.5 ± 6.1 | — | 8.94 ± 3.10 | — |
| *Torulaspora delbrueckii* YIT 8114 | 148.1 ± 19.9** | 23.7 ± 1.9 | 52.5 | 5.30 ± 1.05** | 46.2 |
| *Pichia farinosa* YIT 8054 | 140.6 ± 18.7** | 24.8 ± 4.8 | 60.3 | 4.86 ± 2.07** | 51.8 |
| *Kloeckera africana* YIT 8165 | 143.7 ± 37.5** | 25.4 ± 1.9 | 54.9 | 4.68 ± 1.26** | 54.1 |

**p < 0.01

Through administration of a cholesterol-added high-fat food, the control group exhibited increase in total cholesterol level and elevation of atherosclerotic index to 7.97-9.62. However, the test groups—rats to which a diet containing the yeast cells according to the present invention (10%) had been administered—were found to remarkably suppress elevation of the values in terms of all analyzed items, even though the same high-fat diet was administered. Thus, yeasts; i.e., *Kluyveromyces marxianus* YIT 8292, *Kluyveromyces lactis* YIT 8263, *Hanseniaspora uvarum* YIT 8164, *Issatchenkia orientalis* YIT 8266, *Candida kefyr* YIT 8237, and *Pichia* group in Table 8); the resultant diet was administered to each group consisting of eight rats; with restricted amount (15 g/day) for 14 days.

Table 15 shows the results of plasma lipid analysis. As a result of administration of a high-fat food, the control group exhibited increase in total cholesterol level and elevation of atherogenic index. However, the test groups—rats to which a diet containing the yeast cells according to the present invention (5%) had been administered—were found to remarkably suppress elevation of the values in terms of all analyzed items, even though the same high-fat diet was administered.

TABLE 15

Plasma lipid

| Strains | Total cholesterol (mg/dL) | HDL cholesterol (mg/dL) | Percent reduction of cholesterol (%) | AI (−) | Percent improvement of AI (%) |
|---|---|---|---|---|---|
| Control group (high-fat diet administration group) | 339.7 ± 34.8 | 23.2 ± 3.8 | — | 13.85 ± 1.91 | — |
| Kluyveromyces marxianus YIT 8292 | 205.3 ± 30.1** | 23.6 ± 5.2 | 57.6 | 7.87 ± 1.18** | 46.8 |
| Control group (high-fat diet administration group) | 377.8 ± 75.3 | 21.9 ± 1.9 | — | 16.33 ± 3.83 | — |
| Kluyveromyces lactis YIT 8263 | 222.5 ± 27.2** | 23.9 ± 4.4 | 55.3 | 8.59 ± 2.01** | 50.7 |
| Candida kefyr YIT 8237 | 228.9 ± 69.1** | 25.4 ± 5.0 | 53.0 | 7.98 ± 1.74** | 54.7 |
| Kloeckera africana YIT 8165 | 276.9 ± 54.6** | 25.9 ± 5.2 | 36.1 | 9.89 ± 2.30** | 42.1 |
| Control group (high-fat diet administration group) | 360.0 ± 44.7 | 21.5 ± 5.2 | — | 18.37 ± 6.81 | — |
| Hanseniaspora uvarum YIT 8164 | 237.8 ± 34.8** | 24.2 ± 2.8 | 46.5 | 8.45 ± 2.45** | 57.3 |
| Issatchenkia orientalis YIT 8266 | 241.5 ± 49.6** | 20.9 ± 2.8 | 45.1 | 9.95 ± 1.56** | 48.7 |
|  | 243.3 ± 38.5** | 24.5 ± 3.1 | 44.3 | 8.86 ± 2.09** | 55.0 |
| Control group (high-fat diet administration group) | 284.2 ± 54.1 | 19.9 ± 4.5 | — | 13.66 ± 3.34 | — |
| Torulaspora delbrueckii YIT 8114 | 199.2 ± 37.3** | 21.9 ± 5.3 | 45.4 | 8.63 ± 3.41** | 40.0 |

**$p < 0.01$

Table 16 shows the results of hepatic lipid measurement. In all test groups, the total hepatic cholesterol level decreased significantly, as compared with the control group. Thus, the yeasts according to the present invention have been found to serve as an excellent anti-cholesterol material which exerts an effect of lowering plasma lipid through peroral administration, as well as an effect of lowering hepatic lipid.

TABLE 16

| Strains | Total cholesterol (mg/liver) |
|---|---|
| Control group (high-fat diet administration group) | 538.9 ± 53.5 |
| Kluyveromyces marxianus YIT 8292 | 459.6 ± 44.9** |
| Control group (high-fat diet administration group) | 469.1 ± 54.3 |
| Kluyveromyces lactis YIT 8263 | 370.2 ± 51.1** |
| Candida kefyr YIT 8237 | 368.5 ± 67.1** |
| Kloeckera africana YIT 8165 | 399.5 ± 43.3** |
| Control group (high-fat diet administration group) | 422.2 ± 57.2 |
| Hanseniaspora uvarum YIT 8164 | 390.8 ± 49.1** |
| Issatchenkia orientalis YIT 8266 | 348.5 ± 36.9** |
| Pichia farinosa YIT 8058 | 331.9 ± 40.2** |
| Control group (high-fat diet administration group) | 463.1 ± 66.9 |
| Torulaspora delblueckii YIT 8114 | 380.1 ± 65.4** |

**$p < 0.01$

Example 5

Bile Acid Adsorption Power

Test Method;

For each of cholic acid (CA), taurocholic acid (TCA), glycocholic acid (GCA), chenodeoxycholic acid (CDCA), and deoxycholic acid (DCA), a sodium salt thereof (product of Sigma) was dissolved in a 0.1M phosphate buffer (pH 6.7) or a 0.1M phosphate buffer (pH 7.5) such that the final concentration was adjusted to 1 mM.

Lyophilized cells (100 mg) of *Issatchenkia orientalis* YIT 8266 were placed in a centrifugation tube (15 mL), and each bile acid solution (3.5 mL) prepared above was added thereto. The mixture was shaken (120 spm) at 37° C. One hour later, yeast cells were caused to precipitate through centrifugation (12,000 rpm, 10 minutes), to thereby collect the supernatant. The bile acid contained in the supernatant was quantitated by use of Enzabile II (product of Daiichi Pure Chemicals Co., Ltd.), and percent bile acid adsorption was calculated on the basis of the following formula. As used herein, the term "percent bile acid adsorption" refers to a ratio (%) of the amount of bile acid adsorbed by yeast to the total amount of added bile acid, and the ratio serves as an index of the adsorption strength between the yeast and the bile acid.

percent bile acid adsorption (%)=[{added bile acid (nmol)−bile acid in supernatant (nmol)}/added bile acid (nmol)]×100

Table 17 shows the percent bile acid adsorption. *Issatchenkia orientalis* YIT 8266 has been found to adsorb cholic acid, taurocholic acid, glycocholic acid, or chenodeoxycholic acid, exhibiting excellent primary bile acid adsorption power. The percent adsorption of bile acid by yeast did not depend on the pH (6.7 and 7.2) of the reaction mixture. These results indicate that the yeast tightly binds to primary bile acid in the large intestinal tract and inhibits deconjugation and 7α-dehydroxylation caused by enterobacteria, to thereby inhibit production of secondary bile acid.

In addition, the yeast tightly binds to deoxycholic acid—a type of secondary bile acid. This indicates that, in addition to inhibiting of production of secondary bile acid, the yeast also adsorbs and immobilizes formed secondary bile acid, to thereby reduce the toxicity thereof.

TABLE 17

Percent Bile Acid Adsorption by *Issatchenkia orientalis* (%)

| Yeast | CA pH6.7 | CA pH7.5 | TCA pH7.5 | GCA pH7.5 | CDCA pH7.5 | DCA pH7.5 |
|---|---|---|---|---|---|---|
| *Issatchenkia orientalis* YIT 8266 | 40.3 | 40.2 | 29.3 | 43.8 | 68.8 | 73.7 |

Example 6

In a manner similar to that employed in Example 5, percent adsorption of bile acid by a variety of yeasts was measured. Table 18 shows the results. All of the yeasts exhibited excellent adsorption to bile acids; i.e., chenodeoxycholic acid (primary bile acid) and deoxycholic acid (secondary bile acid).

TABLE 18

Percent Adsorption of Bile Acid by Yeasts

| Strains | YIT No. | Percent adsorption of bile acid (%) | |
| --- | --- | --- | --- |
| | | CDCA (pH7.5) | DCA (pH7.5) |
| Kluyveromyces marxianus | 8292 | 63.0 | 60.0 |
| Kluyveromyces lactis | 8263 | 54.4 | 41.0 |
| Kluyveromyces thermotolerans | 8294 | 79.5 | 53.6 |
| Hanseniaspora uvarum | 8164 | 68.0 | 40.3 |
| Saccharomyces cerevisiae | 8116 | 66.6 | 54.5 |
| Saccharomyces dairensis | 8191 | 50.8 | 44.7 |
| Saccharomyces exiguus | 8109 | 55.5 | 50.4 |
| Saccharomyces unisporus | 8226 | 58.8 | 65.5 |
| Saccharomyces bayanus | 8128 | 61.8 | 64.3 |
| Hyphopichia burtonii | 8299 | 51.6 | 35.3 |
| Candida kefyr | 8237 | 56.2 | 55.3 |
| Candida etchellsii | 8278 | 55.8 | 45.1 |
| Candida zeylanoides | 8018 | 76.1 | 56.0 |
| Candida solani | 8023 | 52.0 | 36.9 |
| Candida maltosa | 8283 | 58.3 | 46.4 |
| Candida tropicalis | 8286 | 58.3 | 40.1 |
| Candida cylindracea | 8276 | 58.8 | 53.0 |
| Candida utilis | 8204 | 51.6 | 42.2 |
| Torulaspora delbrueckii | 8313 | 58.6 | 52.6 |
| Torulaspora delbrueckii | 8133 | 64.6 | 49.4 |
| Pichia anomala | 8297 | 56.4 | 43.4 |
| Pichia anomala | 8298 | 51.6 | 60.9 |
| Pichia holstii | 8038 | 58.8 | 54.6 |
| Zygosaccharomyces rouxii | 8129 | 48.0 | 39.8 |
| Cellulose (Comparative) | — | 4.1 | 3.7 |

Example 7

Inhibition of Secondary Bile Acid Production by Lyophilized Cells of *Issatchenkia orientalis* YIT 8266

Preliminary Test

Male, 5-week-old Wistar rats (obtained from Nihon Kurea) had been bred for 7 days with diet powder F-2 (product of Oriental Yeast). The rats were divided into groups such that no weight difference generates among the groups, each group containing 8 rats. To each group, the diet shown in Table 19 was administered for 14 days. The rats were bred individually in a metal-made cage, and allowed to consume diet and water ad libitum.

TABLE 19

Diet Composition [%]

| Ingredient | Ordinary diet | High-bile-acid diet |
| --- | --- | --- |
| Casein | 22.30 | 22.30 |
| Sucrose | 56.55 | 55.80 |
| Inorganic salt | 4.00 | 4.00 |
| Vitamins | 1.00 | 1.00 |
| Soybean oil | 1.00 | 1.00 |
| Lard | 10.00 | 10.00 |
| Choline bitartrate | 0.15 | 0.15 |
| Cholesterol | 0.00 | 0.50 |
| Sodium cholate | 0.00 | 0.25 |
| Filter paper powder | 5.00 | 5.00 |

After completion of 14 days' breeding, no significant differences in diet consumption and in body weight increase were observed between the ordinary-diet administration group and the high-bile-acid-diet administration group.

Bile Acid Level

Lyophilized feces (day 12 to day 14) (25 mg) were weighed and placed in a test tube (15 mL) equipped with a screw cap, and an internal standard substance (5-β-pregnane-3α,17α,20α-triol) (0.15 μmol) and ethanol (5 mL) were added thereto. The mixture was heated at 70° C. for two hours by means of a block heater. The resultant insoluble matter was precipitated through centrifugation (3,000 rpm, 15 minutes). The supernatant was transferred to another test tube and dried to solid under nitrogen flow. The extract was dissolved in methanol (0.5 mL), and the resultant insoluble matter was removed by means of a filter (0.45 μm) (product of Nihon Millipore Ltd.). An analysis sample (10 μL) was subjected to separation by means of an HPLC system (product of Jasco) under the following conditions.

TABLE 20

Conditions for Separating Bile Acids

| | |
| --- | --- |
| Liquid A: | Acetonitrile/Methanol/30 mM Ammonium acetate (30:30:40) mixture |
| Liquid B: | Acetonitrile/Methanol/30 mM Ammonium acetate (20:20:60) mixture |
| Elution conditions: | Proportional concentration gradient from 100% B + 0% A to 0% B + 100% A over 32 min. followed by elution for 13 min. by use of 100% A. |
| Flow rate: | 1.0 mL/min |
| Column temperature: | 25° C. |

Bilepak-II (4.6 mm i.d.×250 mm) (separation column, product of Jasco)

The eluate provided from a separation column was mixed, at a flow rate of 1.0 mL/minute, with a reaction mixture (0.3 mM β-nicotinamide adenine dinucleotide (β-NAD$^+$), 1 mM ethylenediaminetetraacetic acid, and 10 mM potassium phosphate buffer (pH 7.8) containing 0.05% 2-mercaptoethanol). The liquid mixture was transferred to an enzyme column (Enzymepak (4.6 mm i.d.×35 mm, product of Jasco) charged with 3α-hydroxysteroid dehydrogenase, where NADH (reduced form of β-NAD$^+$) produced upon dehydroxylation of bile acid was monitored by means of a fluorescence detector (excitation wavelength 345 nm, emission wavelength 470 nm).

Each bile acid was identified on the basis of the retention time with reference to the standard. The bile acid concentration was obtained from the corresponding peak area. In this case, percent recovery was corrected by the peak area of the internal standard.

Table 21 shows the results. The results indicate that administration of cholic acid increases the level of primary bile acid reaching the large intestinal tract, to thereby promote production of secondary bile acid. Thus, the effect of a secondary bile acid production inhibitor can be evaluated at high sensitivity.

TABLE 21

Level of Bile Acids Excreted in Feces [μmol/day]

|  | Ordinary diet | High-bile-acid diet |
|---|---|---|
| Primary bile acid |  |  |
| α-Muricholic acid | 1.52 ± 0.35 | 8.52 ± 3.05** |
| β-Muricholic acid | 0.20 ± 0.09 | 8.48 ± 1.55** |
| Hyocholic acid | 0.00 ± 0.00 | 0.23 ± 0.21* |
| Cholic acid | 0.00 ± 0.00 | 29.20 ± 7.44** |
| Chenodeoxycholic acid | 0.00 ± 0.00 | 0.57 ± 0.20** |
| Total primary bile acids | 1.72 ± 0.40 | 47.00 ± 10.31** |
| Secondary bile acid |  |  |
| Deoxycholic acid | 0.72 ± 0.26 | 9.13 ± 5.92** |
| Lithocholic acid | 0.18 ± 0.10 | 0.13 ± 0.18$^{n.s.}$ |
| Hyodeoxycholic acid | 0.01 ± 0.03 | 1.06 ± 0.54* |
| Total secondary bile acids | 0.90 ± 0.35 | 10.32 ± 5.84** |

Note:
Student's t-test
*Significance level 5%
**Significance level 1%
[n.s.] no significance Inhibition of Secondary Bile Acid Production by Lyophilized Cells of *Issatchenkia orientalis* YIT 8266

Lyophylized cells of *Issatchenkia orientalis* YIT 8266 were added to a high-bile-acid diet, and the resultant diet was administered for 14 days (5% mix diet) (Table 22). The energy score of each diet was equalized by controlling the amount of casein, saccharose, lipid, or cellulose. Administration of yeast cells provided substantially no influence on diet consumption and substantially no influence on increase in body weight during the test period (Table 23).

TABLE 22

Diet Composition [%]

| Ingredients | High-bile-acid diet | Yeast-added high-bile-acid diet |
|---|---|---|
| Casein | 22.30 | 20.56 |
| Sucrose | 55.80 | 54.15 |
| Inorganic salt | 4.00 | 4.00 |
| Vitamins | 1.00 | 1.00 |
| Soybean oil | 1.00 | 1.00 |
| Lard | 10.00 | 9.85 |
| Choline bitartrate | 0.15 | 0.15 |
| Cholesterol | 0.50 | 0.50 |
| Sodium cholate | 0.25 | 0.25 |
| Filter paper Powder | 5.00 | 3.55 |
| Heat-dried yeast cells* | 0.00 | 5.00 |

*Issatchenkia orientalis* YIT 8266

TABLE 23

Diet Consumption and Body Weight Increase during Test Period

|  | High-bile-acid diet | Yeast-added high-bile-acid diet |
|---|---|---|
| Diet consumption [g/14 days] | 236.0 ± 8.6 | 227.8 ± 21.5$^{n.s.}$ |

TABLE 23-continued

Diet Consumption and Body Weight Increase during Test Period

|  | High-bile-acid diet | Yeast-added high-bile-acid diet |
|---|---|---|
| Body weight increase [g/14 days] | 95.9 ± 4.0 | 93.6 ± 11.9$^{n.s.}$ |

Note:
Student's t-test
[n.s.] no significance

As shown in Tables 24 and 25, through administration of *Issatchenkia orientalis* YIT 8266, the level of secondary bile acid excreted in feces decreased by approximately 82%, and the secondary bile acid concentration in feces decreased by approximately 84%. This tendency was observed to be particularly remarkable for deoxycholic acid and lithocholic acid. The level of primary bile acid excreted in feces and the primary bile acid concentration in feces were significantly increased through administration of the corresponding cells.

Thus, *Issatchenkia orientalis* YIT 8266 exerted an effect of strongly inhibiting conversion of primary bile acid to secondary bile acid.

TABLE 24

Level of Bile Acids Excreted in Feces [μmol/day]

|  | High-bile-acid diet | Yeast-added high-bile-acid diet |
|---|---|---|
| Primary bile acid |  |  |
| α-Muricholic acid | 13.70 ± 3.40 | 15.27 ± 3.12$^{n.s.}$ |
| β-Muricholic acid | 7.32 ± 2.07 | 11.60 ± 2.48** |
| Hyocholic acid | 0.12 ± 0.17 | 0.29 ± 0.15$^{n.s.}$ |
| Cholic acid | 24.37 ± 5.86 | 35.30 ± 2.55** |
| Chenodeoxycholic acid | 1.10 ± 0.41 | 1.34 ± 0.27$^{n.s.}$ |
| Total primary Bile acids | 46.60 ± 7.30 | 63.80 ± 6.81** |
| Secondary bile acid |  |  |
| Deoxycholic acid | 10.10 ± 6.51 | 0.22 ± 0.46** |
| Lithocholic acid | 0.35 ± 0.31 | 0.00 ± 0.00* |
| Hyodeoxycholic acid | 0.80 ± 0.32 | 1.81 ± 0.64$^{n.s.}$ |
| Total secondary Bile acids | 11.25 ± 6.59 | 2.03 ± 0.81** |

Note:
Student's t-test
*Significance level 5%
**Significance level 1%
[n.s.] no significance

TABLE 25

Composition of Bile Acids in Feces [%]

|  | High-bile-acid diet | Yeast-added high-bile-acid diet |
|---|---|---|
| Primary bile acid |  |  |
| α-Muricholic acid | 23.58 ± 5.32 | 23.11 ± 3.47$^{n.s.}$ |
| β-Muricholic acid | 12.59 ± 3.07 | 17.50 ± 2.51** |
| Hyocholic acid | 0.19 ± 0.27 | 0.43 ± 0.22$^{n.s.}$ |
| Cholic acid | 42.47 ± 11.42 | 53.87 ± 3.01* |
| Chenodeoxycholic acid | 1.89 ± 0.65 | 2.06 ± 0.50$^{n.s.}$ |
| Total primary bile acids | 80.72 ± 11.55 | 96.97 ± 0.98** |
| Secondary bile acid |  |  |
| Deoxycholic acid | 17.30 ± 11.46 | 0.30 ± 0.67** |
| Lithocholic acid | 0.59 ± 0.53 | 0.00 ± 0.00* |

TABLE 25-continued

Composition of Bile Acids in Feces [%]

| | High-bile-acid diet | Yeast-added high-bile-acid diet |
|---|---|---|
| Hyodeoxycholic acid | 1.39 ± 0.59 | 2.73 ± 0.89** |
| Total secondary bile acids | 19.28 ± 11.55 | 3.03 ± 0.98** |

Note:
Student's t-test
*Significance level 5%
**Significance level 1%
n.s.no significance Lowering pH in the Cecum by Lyophilized Cells of *Issatchenkia orientalis* YIT 8266

The contents in the decum (day 14) (0.5 g) were suspended in purified water (4.5 mL), and a 10% aqueous perchloric acid solution (0.5 mL) was added to the suspension. The resultant suspension was stored at 4° C. overnight. The suspension was centrifuged (9,000 rpm, 10 minutes), and the supernatant was collected and passed through a filter (0.45 μm) (product of Nihon Millipore Ltd.). The thus-prepared analysis sample was subjected to HPLC.

Short-chain fatty acids were analyzed by means of an HPLC system (product of Toa Dempa Kogyo) under the following conditions. The pH buffer was mixed with the eluent immediately before passage of the detector.

TABLE 26

Short-Chain Fatty Acid Analysis Conditions

| | |
|---|---|
| Column: | KC-811 Shodex (Showa Denko) × 2 |
| Eluent(flow): | 15 mM Perchloric acid solution containing 7% acetonitrile (1 mL/min) |
| Column temperature: | 42° C. |
| pH-Regulator (flow): | 15 mM Perchloric acid solution containing 7% acetonitrile and 60 mM tris(hydroxymethyl)aminomethane (1 mL/min) |
| Detector: | Conductivity detector (Toa Denpa Kogyo) |
| Cell temperature: | 45° C. |

TABLE 27 pH and Short-Chain Fatty Acid Content in the Cecum

| | High-bile-acid diet | Yeast-added high-bile-acid diet |
|---|---|---|
| pH in the cecum | 6.65 ± 0.08 | 6.46 ± 0.20* |
| Short-Chain Fatty Acid content [mM] | | |
| Acetic acid | 26.6 ± 8.4 | 37.5 ± 4.0** |
| Propionic acid | 7.2 ± 2.3 | 17.5 ± 4.0** |
| Butyric acid | 2.2 ± 1.4 | 3.9 ± 0.8* |
| Lactic acid | 2.5 ± 1.0 | 2.6 ± 1.2 n.s. |
| Succinic acid | 15.5 ± 7.3 | 21.8 ± 7.4 n.s. |
| Formic acid | 1.1 ± 0.6 | 1.8 ± 1.3 n.s. |
| Isobutyric acid | 0.7 ± 0.6 | 0.4 ± 0.4 n.s. |
| Total short-chain fatty acids | 55.9 ± 15.7 | 85.6 ± 5.2** |

Note:
Student's t-test
*Significance level 5%
**Significance level 1%
n.s.no significance High-bile-acid-diet groups exhibited a pH in the cecum of 6.65 and a total amount of short-chain fatty acid of 55.9 mM, whereas yeast (*Issatchenkia orientalis* YIT 8266)-added high-bile-acid-diet groups exhibited a pH in the cecum of 6.46 (significance level 5%) and a total amount of short-chain fatty acid of 85.6 mM (significance level 1%), indicating decrease in pH in the cecum. Thus, the large intestinal pH condition was shifted to more acidic, to thereby deactivate 7α-dehydroxylase of enterobacteria.

Inhibition of Cholesterol Metabolism by Lyophilized Cells of *Issatchenkia orientalis* YIT 8266

Feces (day 14) (25 mg) were weighed and placed in a test tube (15 mL) equipped with a screw cap, and an internal standard substance (5β-cholestane) (0.1 μmol) and a 90% ethanol solution containing 1N sodium hydroxide (1 mL) were added thereto. The mixture was heated at 80° C. by means of a block heater. One hour after, distilled water (0.5 mL) was added, and neutral sterols were taken through two rounds of extraction by use of petroleum ether (2.5 mL). The resultant extract was washed with distilled water (7.5 mL), dehydrated over sodium sulfate, and dried to solid under nitrogen gas flow. The recovered neutral sterols were trimethylsilylated, and analyzed through gas chromatography under the following conditions (Table 28).

TABLE 28

Chromatographic (GC) Analysis Conditions

| | |
|---|---|
| GC apparatus: | Model 5890 (Yokogawa-Hewlett-Packard) |
| Column: | SPB-1 FS-coated capillary glass column (Supelco) 0.32 mm i.d. × 30 m |
| Column temperature: | 250° C., 8 min → 270° C., 10° C./min → 270° C., 15 min |
| Carrier (flow): | He (0.8 mL/min) |
| Injector: | Spilit, T = 230° C. |
| Detector: | FID, T = 280° C. |
| Sample injection: | 1 μL |
| Analysis time: | 25 min |

Through administration of *Issatchenkia orientalis* YIT 8266, the concentrations in feces of coprostanol and coprostanone—decreased cholesterol metabolites in the intestine significantly (Table 29). Since these cholesterol metabolites in the large intestine are related to onset of diseases such as colovectal cancer (Suzuki, K., et al., *Cancer Lett.*, 33, 307-316, 1986), *Issatchenkia orientalis* YIT 8266 is thought to be capable of preventing or treating a variety of diseases, by means of inhibiting production of cholesterol metabolites.

TABLE 29

Neutral Cholesterol Composition in Feces [%]

| | High-bile-acid diet | Yeast-added high-bile-acid diet |
|---|---|---|
| Coprostanol | 25.7 ± 12.5 | 9.2 ± 11.9* |
| Coprostanone | 1.9 ± 2.5 | 0.4 ± 0.6 n.s. |
| Cholesterol | 72.3 ± 14.2 | 90.5 ± 12.4* |
| Coprostanol + Coprostanone | 27.7 ± 14.2 | 9.5 ± 12.4* |

Note:
Student's t-test
*Significance level 5%
n.s.no significance

Example 8

Inhibition of Secondary Bile Acid Production by Cell Contents of *Issatchenkia orientalis* YIT 8266

Preparation of Cell Contents

Lyophilized cells of *Issatchenkia orientalis* YIT 8266 were suspended in a 0.1M phosphate buffer (pH 8.5), and the cells were mechanically ground by means of DYNO-MILL (product of Shinmaru Enterprises). During grinding, 0.45 mm glass beads were employed as a grinding agent, and grinding operation was repeated until grinding of 95% or more cells was confirmed through microscopic observation. The milled cell liquid was centrifuged (9,000 g, 15 minutes)i to thereby isolate cell contents in the supernatant. The cell contents were collected and lyophilized.

Inhibition of Secondary Bile Acid Production by Cell Contents of *Issatchenkia orientalis* YIT 8266

In a manner similar to that employed in Example 7, the effect of the cell contents prepared from *Issatchenkia orientalis* YIT 8266 on inhibition of secondary bile acid production was confirmed.

Table 30 shows the diet composition employed in the test. Administration of yeast cell contents exerted substantially no influence on diet consumption and substantially no influence on increase in body weight during the test period (Table 31).

TABLE 30

Diet Composition (%)

| Ingredients | High-bile-acid diet | Cell-content-added high-bile-acid diet |
|---|---|---|
| Casein | 22.30 | 20.78 |
| Sucrose | 55.80 | 53.12 |
| Inorganic salt | 4.00 | 4.00 |
| Vitamins | 1.00 | 1.00 |
| Soybean oil | 1.00 | 1.00 |
| Lard | 10.00 | 9.77 |
| Choline bitartrate | 0.15 | 0.15 |
| Cholesterol | 0.50 | 0.50 |
| Sodium cholate | 0.25 | 0.25 |
| Filter paper powder | 5.00 | 4.43 |
| Cell contents | 0.00 | 5.00 |

TABLE 31

Diet Consumption and Increase in Body Weight during the Test Period

| | High-bile-acid diet | Cell-content-added high-bile-acid diet |
|---|---|---|
| Diet consumption [g/14 days] | 232.8 ± 9.9 | 220.7 ± 6.5[n.s.] |
| Body weight increase [g/14 days] | 95.9 ± 4.0 | 88.4 ± 4.5[n.s.] |

Note:
Student's t-test
[n.s.] no significance

As shown in Tables 32 and 33, as a result administration of cell contents of *Issatchenkia orientalis* YIT 8266, the level of secondary bile acid excreted in feces decreased by approximately 76%, and the secondary bile acid concentration in feces decreased by approximately 70%.

Thus, similar to the case of lyophilized *Issatchenkia orientalis* YIT 8266, cell contents thereof also exerted an effect of strongly inhibiting conversion of primary bile acid to secondary bile acid.

TABLE 32

Level of Bile Acids Excreted in Feces [μmol/day]

| | High-bile-acid diet | Cell-content-added high-bile-acid diet |
|---|---|---|
| Primary bile acid | | |
| α-Muricholic acid | 8.56 ± 1.85 | 6.80 ± 2.04[n.s.] |
| β-Muricholic acid | 6.80 ± 2.18 | 8.70 ± 3.04[n.s.] |
| Hyocholic acid | 0.20 ± 0.15 | 0.25 ± 0.06[n.s.] |
| Cholic acid | 28.96 ± 11.99 | 29.99 ± 4.77[n.s.] |
| Chenodeoxycholic acid | 0.44 ± 0.29 | 0.64 ± 0.35[n.s.] |
| Total primary bile acids | 44.96 ± 13.17 | 46.37 + 9.40[n.s.] |
| Secondary bile acid | | |
| Deoxycholic acid | 9.87 ± 5.46 | 2.01 ± 2.26** |
| Lithocholic acid | 0.02 ± 0.05 | 0.00 ± 0.00[n.s.] |
| Hyodeoxycholic acid | 0.65 ± 0.36 | 0.49 ± 0.14[n.s.] |
| Total secondary bile acids | 10.54 ± 5.29 | 2.51 ± 2.18** |

Note:
Student's t-test
**Significance level 1%
[n.s.] no significance

TABLE 33

Composition of Bile Acids in Feces [%]

| | High-bile-acid diet | Cell-content-added high-bile-acid diet |
|---|---|---|
| Primary bile acid | | |
| α-Muricholic acid | 16.01 ± 4.33 | 13.75 ± 1.82[n.s.] |
| β-Muricholic acid | 12.39 ± 3.19 | 17.30 ± 3.29** |
| Hyocholic acid | 0.34 ± 0.20 | 0.51 ± 0.09[n.s.] |
| Cholic acid | 51.04 ± 10.63 | 62.47 ± 6.95** |
| Chenodeoxycholic acid | 0.76 ± 0.34 | 1.27 ± 0.56[n.s.] |
| Total primary bile acids | 79.82 ± 8.31 | 94.02 ± 3.61** |
| Secondary bile acid | | |
| Deoxycholic acid | 8.29 ± 8.90 | 3.64 ± 3.76** |
| Lithocholic acid | 0.04 ± 0.11 | 0.00 ± 0.00[n.s.] |
| Hyodeoxycholic acid | 1.13 ± 0.38 | 1.07 ± 0.44[n.s.] |
| Total secondary bile acids | 20.18 ± 8.31 | 5.98 ± 3.61** |

Note:
Student's t-test
**Significance level 1%
[n.s.] no significance

In terms of the total amount of short-chain fatty acid and the pH in the cecum, high-bile-acid-diet groups exhibited a total amount of 54.0 mM and a pH of 6.65, whereas yeast-cell contents-added high-bile-acid-diet groups exhibited a total amount of 68.3 mM (significance level 5%) and a pH of 6.46 (significance level 5%). Thus, the yeast cell contents shifted the large intestinal pH condition to more acidic by increasing the amount of short-chain fatty acid, to thereby deactivate 7α-dehydroxylase of enterobacteria.

TABLE 34 pH and Short-Chain Fatty Acid Content in the Cecum

| | High-bile-acid diet | Cell-content-added high-bile-acid diet |
|---|---|---|
| pH in the cecum | 6.65 ± 0.08 | 6.46 ± 0.20* |
| Short-Chain Fatty | | |

TABLE 34-continued pH and Short-Chain Fatty Acid Content in the Cecum

|  | High-bile-acid diet | Cell-content-added high-bile-acid diet |
|---|---|---|
| Acid content [mM] |  |  |
| Acetic acid | 26.2 ± 9.0 | 30.2 ± 7.1[n.s.] |
| Propionic acid | 7.2 ± 2.5 | 14.3 ± 2.2** |
| Butyric acid | 2.2 ± 1.5 | 2.1 ± 0.9[n.s.] |
| Lactic acid | 2.4 ± 1.0 | 1.9 ± 1.2[n.s.] |
| Succinic acid | 14.3 ± 7.1 | 17.8 ± 6.4[n.s.] |
| Formic acid | 0.9 ± 0.3 | 1.8 ± 1.7[n.s.] |
| Isobutyric acid | 0.7 ± 0.7 | 0.2 ± 0.2[n.s.] |
| Total short-chain fatty acids | 54.0 ± 15.9 | 68.3 ± 13.9* |

Note:
Student's t-test
*Significance level 5%
**Significance level 1%
[n.s.] no significance As a result of administration of cell contents of *Issatchenkia orientalis* YIT 8266, the concentrations in feces of coprostanol and coprostanone—decreased cholesterol metabolites in the intestine significantly. Thus, similar to the case of the lyophilized cells, cell contents of *Issatchenkia orientalis* YIT 8266 are thought to be capable of preventing or treating a variety of diseases by inhibiting production of cholesterol metabolites.

TABLE 35

Neutral Sterol Composition in Feces [%]

|  | High-bile-acid diet | Cell-content-added high-bile-acid diet |
|---|---|---|
| Coprostanol | 21.1 ± 8.2 | 10.0 ± 9.9* |
| Coprostanone | 2.0 ± 1.6 | 0.5 ± 0.5** |
| Cholesterol | 76.9 ± 9.6 | 89.6 ± 10.2* |
| Coprostanol + Coprostanone | 23.1 ± 9.6 | 12.1 ± 10.7* |

Note:
Student's t-test
*Significance level 5%
**Significance level 1%

Example 9

By use of a variety of yeast cells employed in the aforementioned Examples, foods and drinks of the following compositions were produced.

1) Food for Maintaining and Promoting Health (Tablets)

A composition containing the following additives was pelletized, to thereby prepare tablets.

TABLE 36

Composition of Food for Maintaining and Promoting Health [%]

| Dried yeast cells | 10 |
|---|---|
| Plant extract powder | 30 |
| Royal jelly powder | 5 |
| Collagen powder | 5 |
| Lactose | 25 |
| Corn starch | 20 |
| Hydroxypropyl celllose | 4 |
| Mg stearate | 1 |

2) Drink for Maintaining and Promoting Health

A drink for maintaining and promoting health was produced in accordance with the following formulation.

TABLE 37

Composition of Drink for Maintaining and Promoting Health [%]

| Dried yeast cells | 5 |
|---|---|
| Honey | 15 |
| Citric acid | 0.1 |
| dl-Malic acid | 0.1 |
| Plant extract (cinnamon) | 20 |
| D-Solbitol liquid (70%) | 10 |
| Sodium benzoate | 0.05 |
| Flavors | suitable amount |
| Purified water | balance |

3) Fruit-juice-blended Drink

The drink was produced in accordance with the following formulation.

TABLE 38

Composition of Fruit-Juice-Blended Drink [%]

| Glucose liquid sugar | 33 |
|---|---|
| Grapefruit juice | 60 |
| Dried yeast cells | 5 |
| Flavors | suitable amount |
| Sour agent | suitable amount |

4) Fermented Milk

Fermented milk containing heated yeast cells was produced in accordance with the following formulation.

To a sterilized mixture of 10% skimmed milk powder liquid and 5% glucose, a bacterium belonging to *Lactobacillus* was inoculated, to thereby produce yogurt. To the yogurt, heated yeast cells obtained in Example 1 were added in an amount of 0.1-20%, to thereby produce fermented milk.

5) Milk Liquor

To a sterilized mixture of 10% skimmed milk powder liquid and 5% glucose, a bacterium belonging to *Lactobacillus* and heated yeast cells obtained in Example 1 were inoculated simultaneously. The mixture was subjected to stationary culturing at 37° C. for 48 hours, to thereby produce milk liquor.

INDUSTRIAL APPLICABILITY

The cholesterol-lowering agent of the present invention comprising the aforementioned yeast cells or yeast cell contents exerts a remarkable effect of lowering plasma cholesterol and hepatic cholesterol, and therefore is very effective for preventing arteriosclerosis and other diseases caused by accumulation of cholesterol.

The secondary bile acid production inhibitor of the present invention strongly inhibits production of secondary bile acid through adsorption of bile acid, acidic-shift of pH condition in the large intestine, etc., and therefore is very effective for prevention and treatment of colorectal cancer, liver cancer, pancreatic cancer, bile duct cancer, cholelithiasis, etc.

In addition, the yeasts employed in the present invention having no pathogenicity, are considerably safe, as evidenced by these yeasts having been used for producing cheese, koumiss, wine, etc. from ancient times. Thus, the cholesterol-lowering agent of the present invention comprising the yeast cells or yeast cell contents raises no problem when administered for a long period of time. This is confirmed by the finding that no death case has been observed among rats to which the agent had been perorally administered at a dose of 8 g/kg.

Thus, the cholesterol-lowering agent and secondary bile acid production inhibitor of the present invention can be used as a peroral pharmaceutical, and are also very effective for maintaining health and preventing arteriosclerosis, colovectal cancer, liver cancer, pancreatic cancer, bile duct cancer, cholelithiasis, etc. by causing constant consumption of foods containing the agent or inhibitor.

The invention claimed is:

1. A method for lowering cholesterol comprising:
   administering to a subject in need thereof an effective amount of at least one yeast selected from the group consisting of *Issatchenkia*.

2. The method of claim 1, wherein said yeast is administered orally.

3. The method of claim 1, wherein said yeast is administered as live cells.

4. The method of claim 1, wherein said yeast is administered as heated cells.

5. The method of claim 1, wherein said yeast is administered as a lyophilized product.

6. The method of claim 1, wherein said yeast is administered as a milled product.

7. The method of claim 1, wherein said subject has an elevated plasma cholesterol level.

8. The method of claim 1, wherein said subject has a disease or disorder associated with elevated cholesterol levels.

9. The method of claim 1, wherein said subject has hypertriglyceridemia or hyperlipidemia.

10. The method of claim 1, wherein said subject has a cardiovascular disease.

11. The method of claim 1, wherein said subject has atherosclerosis.

* * * * *

UNITED STATES PATENT AND TRADEMARK OFFICE
CERTIFICATE OF CORRECTION

PATENT NO. : 7,413,740 B2  Page 1 of 1
APPLICATION NO. : 11/176398
DATED : August 19, 2008
INVENTOR(S) : Sawada et al.

It is certified that error appears in the above-identified patent and that said Letters Patent is hereby corrected as shown below:

On the title page, Item (75), the seventh Inventor's name is incorrect. Item (75) should read:

-- (75) Inventors: Haruji Sawada, Tokyo (JP); Yasuto Yoshida, Tokyo (JP); Yasue Wada, Tokyo (JP); Kenji Ohishi, Tokyo (JP) Masahiko Itoh, Tokyo (JP); Wakae Yokoi, Tokyo (JP); Tsunekazu Watanabe, Tokyo (JP) --

Signed and Sealed this

Fourteenth Day of October, 2008

JON W. DUDAS
*Director of the United States Patent and Trademark Office*